(12) United States Patent
Ohama

(10) Patent No.: US 6,986,743 B2
(45) Date of Patent: Jan. 17, 2006

(54) ELECTRONIC BLOOD PRESSURE MONITOR

(75) Inventor: Noboru Ohama, Kyoto (JP)

(73) Assignee: Omron Corporation, Kyoto (JP)

( * ) Notice: Subject to any disclaimer, the term of this patent is extended or adjusted under 35 U.S.C. 154(b) by 295 days.

(21) Appl. No.: 10/409,604

(22) Filed: Apr. 9, 2003

(65) Prior Publication Data

US 2004/0002659 A1    Jan. 1, 2004

(30) Foreign Application Priority Data

Apr. 10, 2002  (JP) ............................. 2002-108020

(51) Int. Cl.
*A61B 5/02*       (2006.01)
(52) U.S. Cl. ...................... 600/490; 600/485; 600/500
(58) Field of Classification Search ......... 600/485–507
See application file for complete search history.

(56) References Cited

U.S. PATENT DOCUMENTS 4,009,709 A * 3/1977 Link et al. .................. 600/494
4,712,563 A * 12/1987 Link .......................... 600/494
5,156,158 A * 10/1992 Shirasaki .................... 600/493
6,805,670 B2 * 10/2004 Shirasaki .................... 600/490

FOREIGN PATENT DOCUMENTS

JP          2002-53671        2/2002

* cited by examiner

*Primary Examiner*—Max F. Hindenburg
*Assistant Examiner*—Patricia C. Mallari
(74) *Attorney, Agent, or Firm*—Morrison & Foerster LLP

(57) ABSTRACT

At the time of measuring a blood pressure, when an MPU controls a pressure in a cuff, detects a pulse wave generated due to pressurizing of a cuff pressure via a band-pass filter or the like, calculates a wave feature value of the detected pulse wave and calculates the blood pressure so as to output it using the calculated wave feature value, the MPU detects the pulse wave in a range of the cuff pressure where the pule wave can be detected. Therefore, since a blood pressure measuring process constituted of detection of the pulse wave, calculation of the wave feature value and calculation of the blood pressure is executed within the range of the cuff pressure where the pulse wave can be detected, the process is prevented from being executed within a range where the pulse wave cannot be detected, thereby measuring the blood pressure with good accuracy.

27 Claims, 9 Drawing Sheets

Fig. 6A PULSE WAVE AMPLITUDE Am

Fig. 6B RELATIVE WAVE WIDTH Rw=Tw/T×100

Fig. 6C RELATIVE MINIMUM TILT Dfn

Fig. 6D WAVE AVERAGE VALUE Rav=Ma/Am×100

ELECTRONIC BLOOD PRESSURE MONITOR

BACKGROUND OF THE INVENTION

1. Field of the Invention

The present invention relates to an electronic blood pressure monitor for determining a blood pressure value using a pulse wave and, more particularly, to an electronic blood pressure monitor for determining a blood pressure value based on a wave feature value of the wave pulse.

2. Description of the Related Art

In a blood pressure measuring method using a conventional electronic blood pressure monitor, a blood pressure measuring method using one pulse wave is suggested. This method calculates a blood pressure according to a probability density function for defining a relationship between a wave feature value such as an average level and a peak width of a pulse waveform actually measured based on a waveform of a pulse wave detected originally based on pressure oscillation generated when a cuff is attached to an upper arm portion and the cuff is pressured, namely, a pulse wave component of a volumetric change of an artery, and a relative cuff pressure based on a blood pressure value. This method does not require a new measuring system and an input signal, and can calculate a blood pressure based on a pulse wave signal of only one pulse. The blood pressure value is calculated at a pressure level of an arbitrary one point in entire interval of a pressure to be applied to the cuff.

However in such a conventional electronic blood pressure monitor, since also a portion at a low level of a pulse wave signal is used for calculating a blood pressure value, a noise component included in the detected pulse wave signal becomes large, and an S/N ratio becomes small. As a result, in the detection of the pulse wave, the calculation of the wave feature value of a pulse wave and calculation of the blood pressure value based on the calculated wave feature value, an error factor becomes large. As a result, it is difficult to obtain a blood pressure value with high accuracy.

SUMMARY OF THE INVENTION

It is therefore an object of the present invention to provide an electronic blood pressure monitor capable of improving blood pressure measuring accuracy.

An electronic blood pressure monitor according to an aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the cuff; a wave feature calculating unit for calculating a wave feature value of the pulse wave detected by the pulse wave detector; a function memory that stores a two-parameter function having the wave feature value and a relative cuff pressure as parameters, the relative cuff pressure being a pressure difference between the detected cuff pressure and a blood pressure of the subject; a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter; a relative cuff pressure determining unit that determines the relative cuff pressure corresponding to the pulse wave detected by the pulse wave detector as a maximum of the single-parameter function or a maximum of a function generated based on the single-parameter function; and a blood pressure calculating unit that calculates the blood pressure of the subject by subtracting the determined relative cuff pressure from the cuff pressure detected by the pressure detector when the pulse wave detector detects the pulse wave. The cuff pressure controller maintains the cuff pressure between an upper limit and a lower limit while the pulse wave detector detects the pulse wave.

Therefore, the pulse wave is detected by the pulse wave detector, the wave feature value of the pulse wave is calculated by the wave feature calculating unit, and a blood pressure value is estimated by the blood pressure calculating unit in such a manner that the cuff pressure is controlled within a range where the cuff pressure does not exceed the upper limit and is not less than the lower limit. For this reason, when the cuff pressure exceeds the upper limit or is less than the lower limit, the pulse wave contains a noise component. However, since the cuff pressure is controlled within the range between the upper limit and the lower limit, the noise component is prevented from effecting the measurement, thereby improving blood pressure measuring accuracy.

In addition, since the upper limit is provided, excessive pressurizing is prevented, and thus pain of the subject caused by the excessive pressurizing can be reduced.

An electronic blood pressure monitor according to another aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the cuff; a wave feature calculating unit for calculating a wave feature value of the pulse wave detected by the pulse wave detector; a function memory that stores a two-parameter function having the wave feature value and a relative cuff pressure as parameters, the relative cuff pressure being a pressure difference between the detected cuff pressure and a blood pressure of the subject; a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter; a relative cuff pressure determining unit that determines the relative cuff pressure corresponding to the pulse wave detected by the pulse wave detector as a maximum of the single-parameter function or a maximum of a function generated based on the single-parameter function; a blood pressure calculating unit that calculates the blood pressure of the subject by subtracting the determined relative cuff pressure from the cuff pressure detected by the pressure detector when the pulse wave detector detects the pulse wave; and a blood pressure averaging unit that calculates an average blood pressure. The cuff pressure controller changes the cuff pressure so that the cuff pressure approaches the average blood pressure when the average blood pressure is not equal to the cuff pressure detected by the pressure detector when the pulse wave detector detects the pulse wave, and the pulse wave detector detects the pulse wave at the cuff pressure changed by the cuff controller.

Therefore, since the pulse wave has approximately maximum amplitude of the pulse wave generated at the average blood pressure or in its vicinity and a high S/N ratio, accuracy of blood pressure estimation is improved.

An electronic blood pressure monitor according to still another aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the duff; a wave feature calculating unit for calculating a wave feature value of the pulse wave detected by the pulse wave detector; a function memory that stores a two-parameter function having the wave feature value and a relative cuff pressure as parameters, the relative cuff pressure being a pressure difference between the detected cuff pressure and a blood pressure of the subject; a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter; a relative cuff pressure determining unit that determines the relative cuff pressure corresponding to the pulse wave detected by the pulse wave detector as a maximum of the single-parameter function or a maximum of a function generated based on the single-parameter function; and a blood pressure calculating unit that calculates the blood pressure of the subject by subtracting the determined relative cuff pressure from the cuff pressure detected by the pressure detector when the pulse wave detector detects the pulse wave. The electronic blood pressure monitor uses the calculated blood pressure of the subject to evaluate the cuff pressure detected by the pressure detector when the pulse wave detector detects the pulse wave, changes the cuff pressure to an appropriate value and calculates the blood pressure of the subject at the changed cuff pressure.

Therefore, the cuff pressure which is suitable for estimating the blood pressure changes according to subjects, conditions of one subject and measuring time, but since the cuff pressure which is suitable for measuring the blood pressure is detected at every time of measurement, the high blood pressure measuring accuracy can be obtained regardless of dispersion such as subjects, conditions of one subject and measuring time.

An electronic blood pressure monitor according to yet another aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the cuff; a wave feature calculating unit for calculating a wave feature value of the pulse wave detected by the pulse wave detector for each of a systolic blood pressure and a diastolic blood pressure; a function memory that stores, for each of the systolic blood pressure and the diastolic blood pressure, a two-parameter function having the wave feature value and a relative cuff pressure as parameters, the relative cuff pressure being a pressure difference between the detected cuff pressure and a blood pressure of the subject; a single-parameter function generating unit that generates a single-parameter function for each of the systolic blood pressure and the diastolic blood pressure by setting the wave feature value of the corresponding two-parameter function at the corresponding calculated wave feature value of the pulse wave detected by the pulse wave detector so that the single-parameter functions have the relative cuff pressure as a parameter; a relative cuff pressure determining unit that determines, for each of the systolic blood pressure and the diastolic blood pressure, the relative cuff pressure corresponding to the pulse wave detected by the pulse wave detector as a maximum of the single-parameter function or a maximum of a function generated based on corresponding the single-parameter function; a blood pressure calculating unit that calculates, for each of the systolic blood pressure and the diastolic blood pressure, the blood pressure of the subject by subtracting the determined relative cuff pressure from the corresponding cuff pressure detected by the pressure detector when the pulse wave detector detects the pulse wave, the blood pressure calculating unit calculating a systolic and diastolic average by averaging the calculated blood pressure corresponding to the systolic blood pressure and the calculated blood pressure corresponding to the diastolic blood pressure, and a blood pressure averaging unit. The electronic blood pressure monitor repeats the calculation of the blood pressure of the subject at a plurality of the cuff pressures for each of the systolic blood pressure and the diastolic blood pressure, the blood pressure averaging unit calculates an average of the blood pressure of the subject calculated at the plurality of the cuff pressures for each of the systolic blood pressure and the diastolic blood pressure such that a higher weight is given to the calculated blood pressure having the corresponding systolic and diastolic average closer to the cuff pressure of the corresponding pulse wave detection.

Therefore, an attention is paid to that as the cuff pressure at the time of detecting the pulse wave is closer to the corresponding average blood pressure (a difference between them is smaller), the amplitude of the pulse wave is larger (the S/N ratio is larger and the error is smaller), and the weight is increased so that a value with less error affects effectively the calculation in the blood pressure calculating unit. For this reason, the accuracy of estimating the blood pressure value can be improved.

An electronic blood pressure monitor according to yet another aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the cuff; a wave feature calculating unit for calculating a wave feature value of the pulse wave detected by the pulse wave detector; a function memory that stores a two-parameter function having the wave feature value and a relative cuff pressure as parameters, the relative cuff pressure being a pressure difference between the detected cuff pressure and a blood pressure of the subject; a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter; a relative cuff pressure determining unit that determines the relative cuff pressure corresponding to the pulse wave detected by the pulse wave detector as a maximum of the single-parameter function or a maximum of a function generated based on the single-parameter function; a blood pressure calculating unit that calculates the blood pressure of the subject by subtracting the determined relative cuff pressure from the cuff pressure detected by the pressure detector when the pulse wave detector detects the pulse wave; and a blood pressure averaging unit. The electronic blood pressure monitor repeats the calculation of the blood pressure of the subject at a plurality of the cuff pressures, the blood pressure averaging unit calculates an average of the blood pressures of the subject calculated at the plurality of the cuff pressures such that a higher weight is given to the blood pressure calculated from the pulse wave having a greater amplitude.

Therefore, the weight is increased so that as the level of the pulse wave amplitude is larger, in other words, the S/N ratio is larger and the error is smaller, the value with less error affects effectively the calculation in the blood pressure calculating unit. For this reason, the accuracy of estimating the blood pressure value can be improved.

An electronic blood pressure monitor according to yet another aspect of the present invention includes: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressured by the cuff; a wave feature calculating unit for calculating a wave feature value of the pulse wave detected by the pulse wave detector; a function memory that stores a two-parameter function having the wave feature value and a relative cuff pressure as parameters, the relative cuff pressure being a pressure difference between the detected cuff pressure and a blood pressure of the subject; a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter; a relative cuff pressure determining unit that determines the relative cuff pressure corresponding to the pule wave detected by the pulse wave detector as a maximum of the single-parameter function or a maximum of a function generated based on the single-parameter function; and a blood pressure calculating unit that calculates the blood pressure of the subject by subtracting the determined relative cuff pressure from the cuff pressure detected by the pressure detector when the pulse wave detector detects the pulse wave. The cuff pressure controller and the pressure detector operate to increase the cuff pressure to a predetermined pressure with a predetermined tolerance.

For this reason, it is not necessary to exactly control the cuff pressure to a specified pressurizing target value at the time of measuring the blood pressure, and since the control may be made within a predetermined tolerance, high-speed pressurizing becomes possible, thereby shortening the measuring time.

DESCRIPTION OF THE PREFERRED EMBODIMENTS

An electronic blood pressure monitor according to an embodiment detects one or more pulse waves and calculates a wave feature value for detected each pulse wave so as to calculate a blood pressure value based on the calculated wave feature values. In the detection of the pulse wave, a upper limit and a lower limit are set and a cuff pressure is adjusted within their interval, and a pulse wave, which is detected in a vicinity of a maximum average blood pressure (average blood pressure or a blood pressure in its vicinity), namely, in a vicinity where an amplitude of the pulse wave becomes maximum and an S/N ratio becomes maximum during the blood pressure measurement, is used for calculating the blood pressure value, and while a pressurizing operation and a pressure reducing operation on the cuff are being repeated, the blood pressure is variably adjusted to a pressurizing level suitable for blood pressure measurement, namely, a pressurizing level at which the amplitude of the pulse wave becomes maximum so as to be measured. In such a manner, the blood pressure measuring accuracy is improved.

Here, the interval between the upper limit and the lower limit is within a range of the cuff pressure level at which the pulse wave can be detected, preferably within a range of the cuff pressure level at which the pulse wave with less noise can be detected.

[Structure of the Electronic Blood Pressure Monitor]

Figure 1:
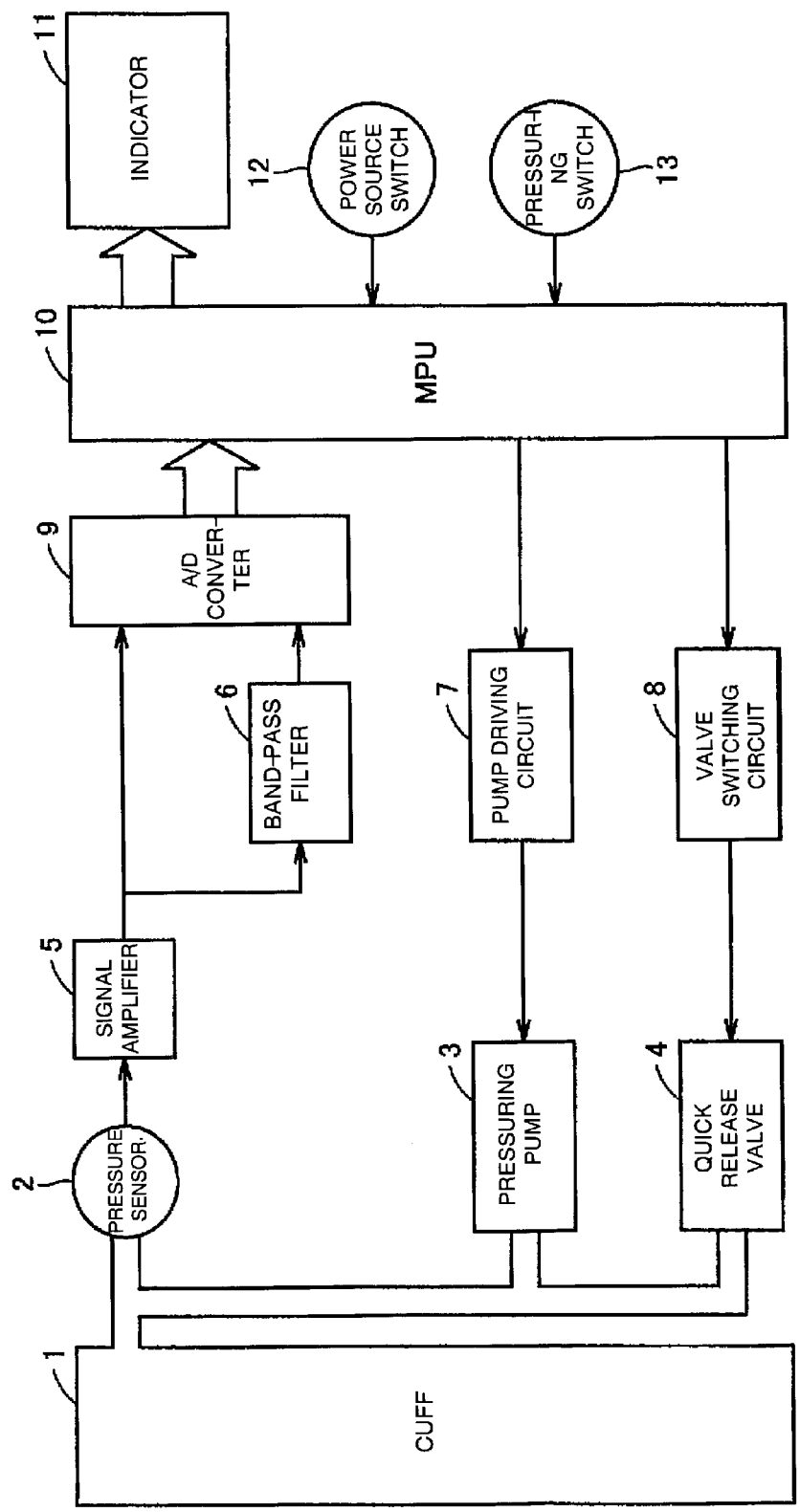
FIG. 1 is a block diagram of an electronic blood pressure monitor according to an embodiment.

The structure of the electronic blood pressure monitor according to the embodiment will be explained with reference to FIG. 1. The cuff 1 is attached to a portion of an organism to be measured and pressures an artery. The pressure sensor 2 detects a cuff pressure. The pressurizing pump 3 pressures the cuff 1 so as to raise the cuff pressure. The quick release valve 4 quickly releases an air in the cuff 1 so as to quickly reduce the cuff pressure. The signal amplifier 5 amplifies a signal of the cuff pressure output from the pressure sensor 2. The band-pass filter 6 takes out a pulse wave from the signal of the cuff pressure output from the signal amplifier 5. The pump driving circuit 7 drives the pressurizing pump 3. The valve open/close circuit 8 opens and closes the quick release valve 4. The A/D converter inputs an analog signal of the amplified cuff pressure output from the signal amplifier 5 so as to convert this signal into a digital signal and outputs the digital signal to an MPU (Microprocessor unit) 10. The indicator 11 indicates a blood pressure value or the like calculated by the MPU 10. The power source switch 12 is operated in order to turn on/off a power source of the electronic blood pressure monitor. The pressurizing switch 13 is operated in order to start pressurizing of the cuff 1. The MPU 10 controls the pump driving circuit 7 for the pressurizing pump 3, the valve open/close circuit 8 for the quick release valve 4, the indicator 11 and the like.

[Blood Pressure Measuring Operation in the Embodiment]

Figure 2:
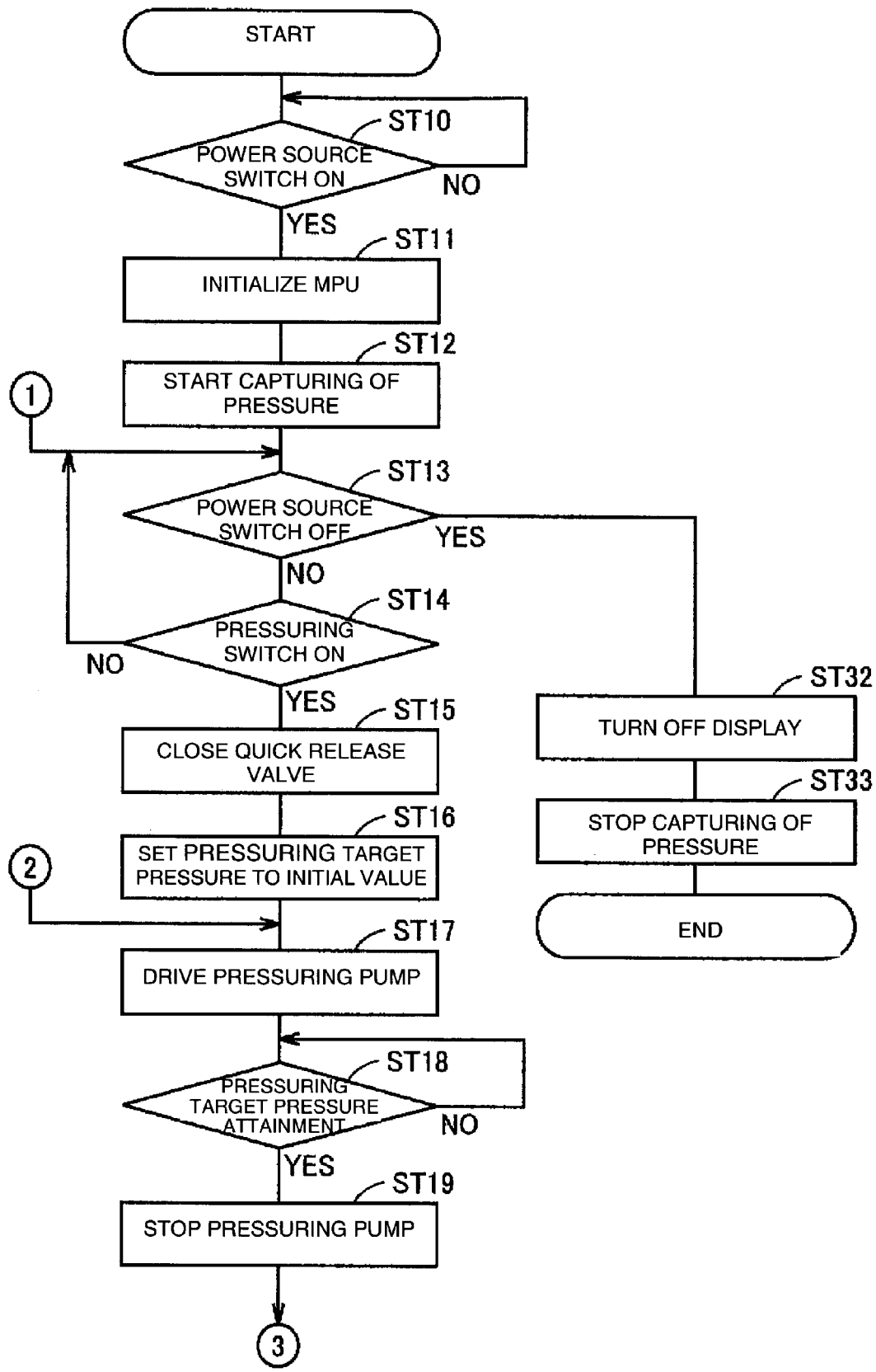
FIG. 2 is an operational flowchart of the electronic blood pressure monitor according to the embodiment.

The blood pressure measuring operation according to the electronic blood pressure monitor in FIG. 1 will be explained below according to the flowcharts in FIGS. 2 to 4 with reference to a flowchart of FIG. 5 in the case where the level of the cuff pressure corresponding to lapse of measuring time is changed gradually.

When the power source switch 12 is pushed down (step ST (hereinafter, referred to as ST) 10), the MPU 10 initializes internal RAM, port, timer and the like, not shown, into a state that a blood pressure can be measured (ST 11). The MPU 10 starts capturing of data of a cuff pressure transmitted from the pressure sensor 2 via the signal amplifier 5 and the A/D converter 9 (ST 12).

The MPU 10 always monitors whether the power source switch 12 and the pressurizing switch 13 are pushed down (ST 13, ST 14). When the MPU 10 detects that the pressurizing switch 13 is pushed down, it outputs a valve closing signal to the valve open/close circuit 8 so that the quick release valve 4 is closed (ST 15). A pressurizing target pressure of an arbitrary predetermined level is set to an initial value (for example, 100 mmHg) (ST 16). A value of the pressurizing target pressure is a level when the cuff pressure is changed as shown in FIG. 5, and can be arbitrarily changed. The value of the pressurizing target pressure is, as shown in FIG. 5, set within the interval between the upper limit and the lower limit.

The above-mentioned level of the pressurizing target pressure does not have to be precise, and some arbitrary allowance, for example, +10 mmHg may be set for the pressurizing target pressure of a predetermined level.

Since the MPU 10 outputs a pump driving signal to the pump driving circuit 7, the pump driving circuit 7 drives the pressurizing pump 3. As a result, at time t1 in FIG. 5, the cuff 1 is pressured (ST 17). The MPU 10 sequentially inputs a current cuff pressure output from the pressure sensor 2 and always compares the input current cuff pressure with the pressurizing target pressure (ST 18). As a result of the comparison, when the MPU 10 detects that the current cuff pressure is not less than the pressurizing target pressure at time t2 in FIG. 5, the MPU 10 outputs a pump stopping signal to the pump driving circuit 7. For this reason, the pressurizing pump 3 is stopped, and the pressurizing of the cuff is stopped (ST 19).

After the pressurizing is stopped, the MPU 10 waits for the current cuff pressure being stable, and detects (inputs) data of a pulse wave filtered from the signal of the cuff pressure via the band-pass filter 6 and the A/D converter 9 (ST 20). A number of the pulse waves to be detected may be not less than one. Here, for example, the number is three. The MPU 10 extracts a wave feature value of each detected pulse wave according to a pulse wave feature value extracting algorithm (ST 21). The pulse wave feature value extracting algorithm will be mentioned later.

A value of systolic blood pressure (hereinafter, SBP) and a value of a diastolic blood pressure (hereinafter DBP) are calculated based on the feature value for each extracted pulse wave according to a blood pressure value calculating algorithm (ST 22).

Next, the MPU 10 judges whether the calculated SBP and DBP are normal (ST 23). Concretely, in the case where a difference between a maximum value and a minimum value of the SBPs calculated for the detected pulse waves is not more than a reference value, the calculated SBP is judged as the normal value. Here, the reference value is supposed to be 5 mmHg, but this value is not limited to this. Similarly in the case where a difference between a maximum value and a minimum value of the DBPs calculated for the pulse waves is not more than a reference value, the calculated DBP is judged as a normal value. Here, the reference value is supposed to be 5 mmHg, but this value is not limited to this. In the case where both the calculated SBP and DBP are judged as the normal values, the calculated blood pressure value shown by the SBP and DBP is judged as the normal value (ST 23).

A judgment is made where first blood pressure measurement or re-measurement (ST 24). When the judgment is made as the first measurement, a judgment is made whether the calculated blood pressure value is the normal value or an abnormal value (not the normal value) (ST 25). When the calculated blood pressure value is the normal value, an average value of the SBPs calculated for the detected pulse waves is obtained. The obtained average value is a result value of the SBP. Moreover, an average value of the DBPs calculated for the pulse waves is obtained, and the average value is a result value of the DBP (ST 26). A pulse rate is calculated according to a publicly-known procedure (ST 27).

The result value of the SBP, the result value of the DBP and the calculated pulse rate are indicated on the indicator 11 (ST 28). The release target pressure is set to an initial value (ST 29). This value is changeable, and here for example, it is 5 mmHg.

Since the MPU 10 outputs a valve opening signal to the valve open/close circuit 8, the quick release valve 4 is opened (ST 30). As a result, the cuff pressure of the cuff 1 quickly reduces. The MPU 10 sequentially inputs a current cuff pressure output from the pressure sensor 2, and always compares the input current cuff pressure with the release target pressure (ST 31).

As a result of the comparison, when the current cuff pressure is not more than the release target pressure, the MPU 10 returns to a state where it always monitors whether the power source switch 12 and the pressurizing switch 13 are pushed down (ST 13). When the power source switch 12 is pushed down, the MPU 10 turns off the indicator 11 (ST 32), and stops capturing the data of the cuff pressure from the pressure sensor 2 (ST 33). As a result, a series of the blood pressure measurement is ended.

Figure 3:
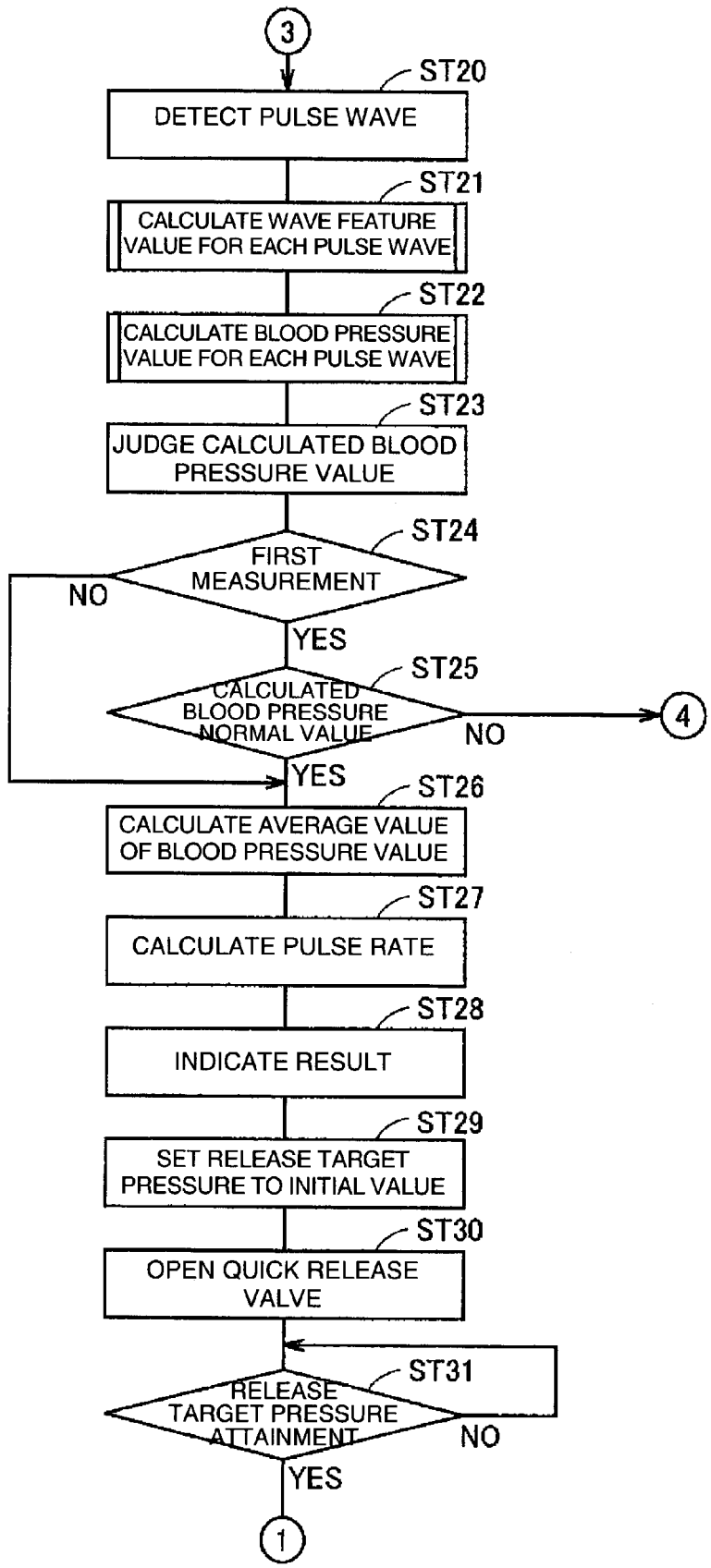
FIG. 3 is an operational flowchart of the electronic blood pressure monitor according to the embodiment.
Figure 4:
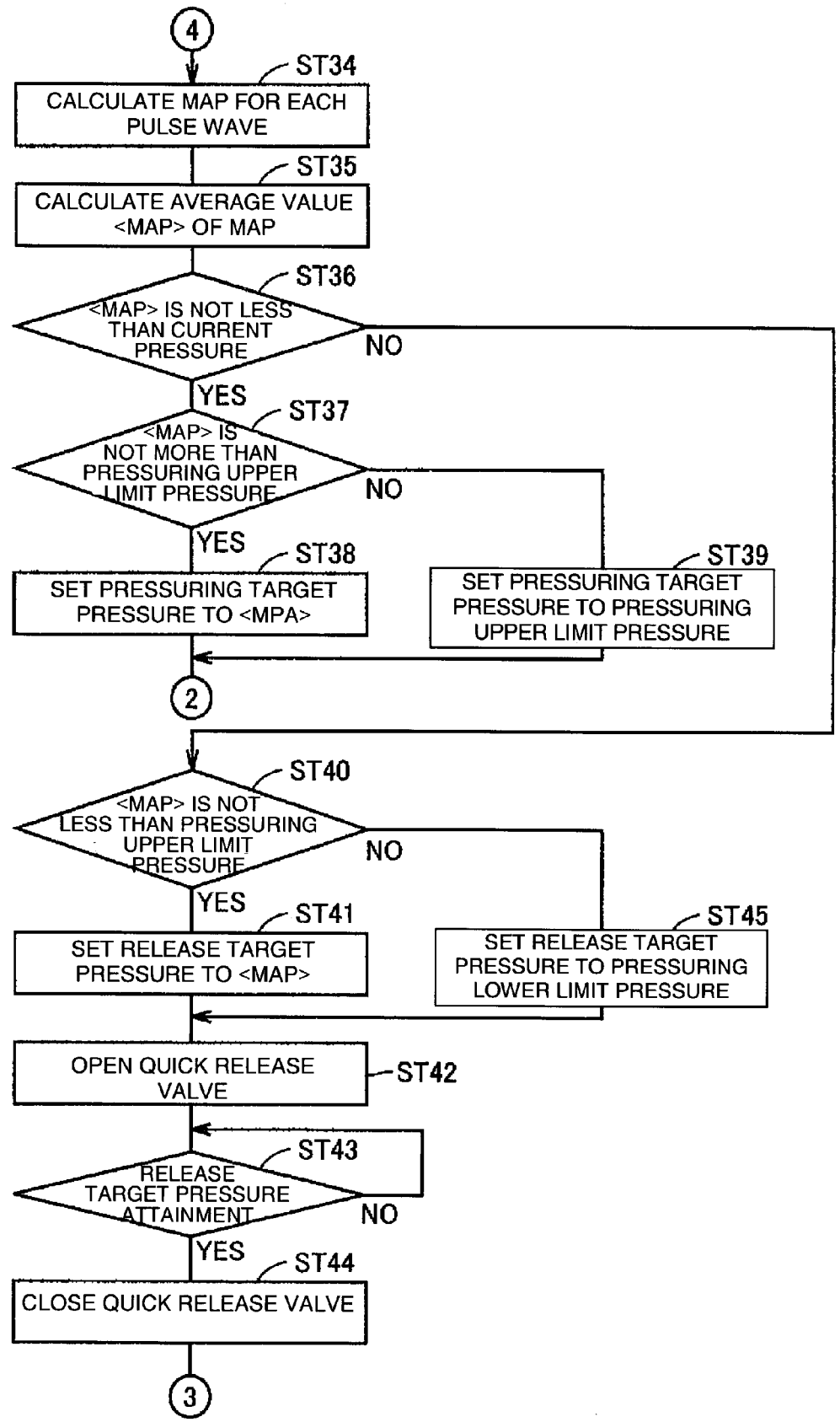
FIG. 4 is an operational flowchart of the electronic blood pressure monitor according to the embodiment.

When the blood pressure value calculated at the first measurement is the abnormal value, the pressurizing target pressure is reset so that the re-measurement is executed according to the flowchart in FIG. 3. In the flowchart of FIG. 3, the MPU 10 calculates an average blood pressure for each pulse wave (hereinafter, MAP) from the SBPs and DBPs calculated at ST 22 for the pulse waves detected at ST 20 (ST 34). Here, the MAP is calculated according to the following equation:

$$MAP = DBP + ((SBP-DBP)/3) \qquad \text{Equation (1)}.$$

The equation (1) is publicly known. Two MAPs having the close values calculated for the pulse waves are taken out, and an average value of the taken out two MAPs (hereinafter, <MAP>) is calculated (ST 35). When the levels of the cuff pressures detected correspondingly to the pulse waves are different, the MPU 10 calculates the <MAP> utilizing a weighted average of a following equation (2). In the equation (2), a parameter a [i] designates a weight, and as the amplitude of the corresponding pulse wave is larger, the <MAP> becomes larger, and as the amplitude is smaller, the <MAP> becomes smaller.

$$<MAP> = \sum_{i=1}^{2} a[i] \, MAP \, [i] \qquad \text{Equation (2)}$$

The MPU 10 compares the calculated <MAP> with the value of the input current cuff pressure (ST 36). As a result of the comparison, when <MAP> is judged as not being not less than the current cuff pressure value, the procedure goes to ST 40, mentioned later, but when the <MAP> is judged as being not less than the current cuff pressure value, since the current cuff pressure is low, <MAP> is compared with the upper limit (for example, 130 mmHg) (ST 37).

As a result of the comparison, when <MAP> is judged as being not more than the upper limit (does not exceed the upper limit), the MPU 10 changes to set the pressurizing target pressure to <MAP> (ST 38) so that the current cuff pressure approaches the average blood pressure, in other words, the pulse wave amplitude becomes maximum. When the <MAP> is judged as not being not more than the upper limit (being not less than the upper limit), the MPU 10 changes to set the pressurizing target pressure to the upper limit (ST 39) so that the current cuff pressure approaches the average blood pressure, in other words, the pulse wave amplitude becomes maximum.

After the pressurizing target pressure is changed to be set, the pressurizing pump 3 is driven and the cuff pressure is raised to the changed pressurizing target pressure (ST 17). At this time, the cuff pressure rises to a direction of an arrow A in FIG. 5. Similarly, when the cuff pressure is pressured to the changed pressurizing target pressure (<MAP> calculated at the last time), the cuff pressure is held in a vicinity of the pressurizing target pressure (the pressurizing target pressure or a pressure in its vicinity) (ST 18, ST 19), and the blood pressure is detected, the pulse wave feature value is calculated and the blood pressure value is calculated based on the calculated feature value (ST 20 to ST 22).

On the other hand, when <MAP> is less than the current cuff pressure (NO at ST 36), <MAP> is compared with the lower limit (ST 40). As a result of the comparison, when <MAP> is less than the lower limit, the release target pressure is changed to be set to the lower limit (ST 45), but when <MAP> is not less than the lower limit, the release target pressure is changed to be set to <MAP> (ST 41).

Since the MPU 10 outputs the valve opening signal to the valve open/close circuit 8 so that the current cuff pressure is reduced to the changed release target pressure, the quick release valve 4 is opened (ST 42). As a result, the cuff pressure abruptly reduces. At this time, the cuff pressure drops to a direction of an arrow B in FIG. 5. The MPU 10 sequentially inputs the current cuff pressure detected via the pressure sensor 2, and always compares the input current cuff pressure with the release target pressure (ST 43). When the current cuff pressure is not more than the release target pressure (YES at ST 43), since the MPU 10 outputs the valve closing signal to the valve open/close circuit 8, the quick release valve 4 is closed (ST 44). As a result, the cuff pressure is held in the vicinity of the release target pressure (the release target pressure or a pressure in its vicinity), and the pulse wave is detected, the pulse wave feature value is calculated based on the detected pulse wave and the blood pressure value is calculated based on the calculated wave feature value (ST 20 to ST 22).

As mentioned above, the detection of the pulse wave, the calculation of the pulse wave feature value and the calculation of the blood pressure value based on the calculated wave feature value are carried out in an interval between the set upper limit and lower limit. Moreover, in the detection of the pulse wave, the calculation of the wave feature value of the detected pulse wave and the calculation of the blood pressure value based on the calculated wave feature value, the pressurizing set value is changeably set so that the pulse wave, which is detected in a vicinity of the average blood pressure (the average blood pressure or a blood pressure in its vicinity, and the blood pressure in a vicinity where the pulse wave amplitude becomes maximum), is used, and the cuff pressure is adjusted to the set pressurizing set value. Thereafter, the pulse wave is detected in the cuff pressure held in the vicinity of the pressurizing set value.

Figure 5:
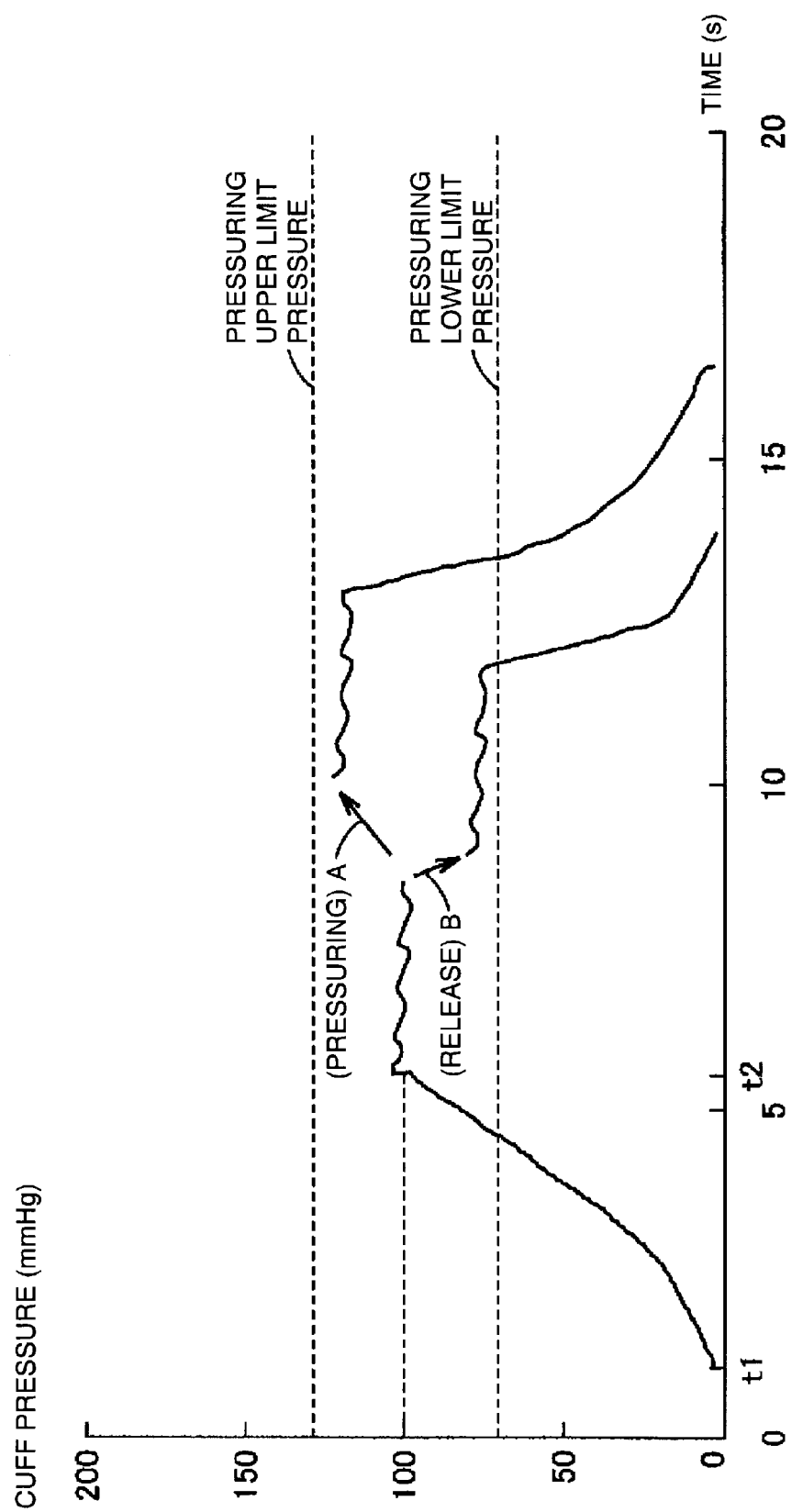
FIG. 5 is a diagram showing a sequence of cuff pressure adjustment according to the embodiment.
Figure 6:
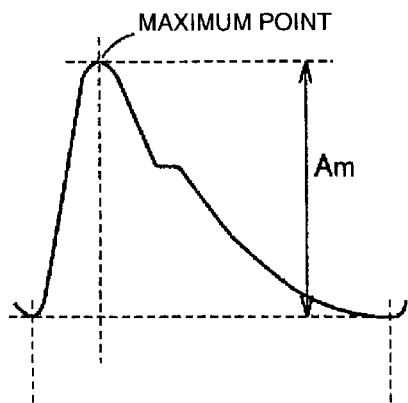
FIGS. 6A to 6D are diagrams explaining a pulse wave feature value according to the embodiment.
Figure 6:
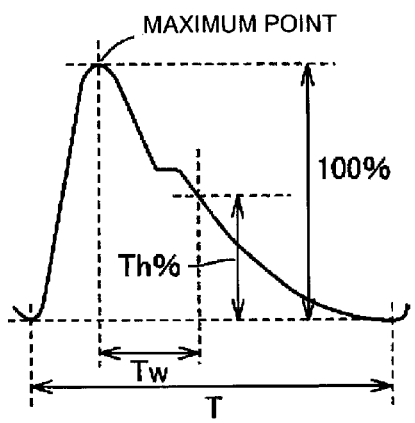
Figure 6:
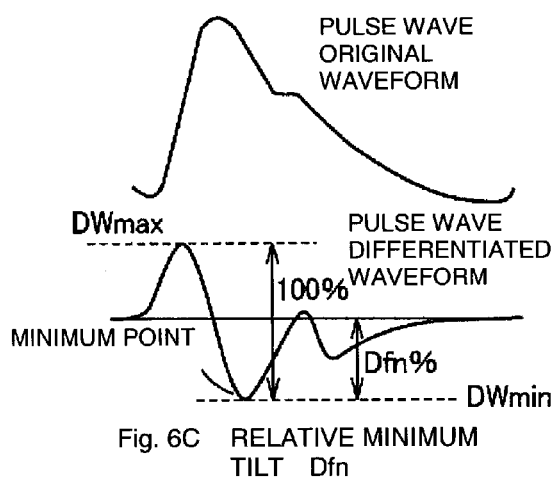
Figure 6:
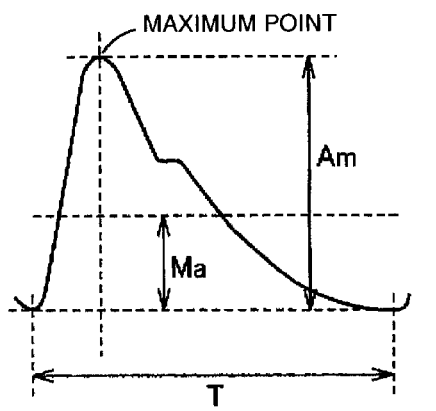

A level of the range between the upper limit and the lower limit in FIG. 5 may be set during the blood pressure measurement so as to be different from a level at the time of starting the blood pressure measurement. Namely, the range is preferably such that the pulse wave can be detected more properly during the blood pressure measurement.

The calculating algorithm of the pulse wave feature value (ST 21) will be explained below with reference to FIGS. 6A to 6D. Here, the wave feature values which show the features of the four kinds of the pulse waves for each detected pulse wave, namely, a pulse wave amplitude Am, a relative wave width Rw, a relative minimum tilt Dfn and a wave average value Rav are calculated. However, the wave feature value to be calculated is not limited to this four kinds. Moreover, the wave feature values to be calculated may be not less than one kind. Calculating equations of the four kinds of the wave feature values are shown below.

$$Am = PW\max - PW\min \qquad \text{Equation (3)}$$

$$Rw = \frac{Tw}{T} \times 100 \qquad \text{Equation (4)}$$

$$Dfn = \frac{DW\max - DW\min}{DW\min} \times 100 \qquad \text{Equation (5)}$$

$$Rav = \frac{Ma}{Am} \times 100 \qquad \text{Equation (6)}$$

$$Ma = \frac{\int_0^T PW(t)\,dt}{T} \qquad \text{Equation (7)}$$

In the equation 3, a parameter PWmax is an amplitude maximum value of one pulse wave, and a parameter PWmin is an amplitude minimum value of one pulse wave.

In the equation 4, a parameter T is a period of one pulse wave, and a parameter Tw is time at which the wave value drops from a maximum point to a variable level Th. The level Th can be arbitrarily changed as a ratio with respect to the amplitude Am between the wave maximum point and minimum point.

In the equation 5, a parameter DWmax is a maximum value of a waveform when one pulse wave is differentiated so that a pulse wave differentiated waveform is generated. Similarly, a parameter DWmin is a minimum value of the pulse wave differentiated waveform.

In the equation 6, a parameter Ma is an average value of one pulse wave, and it is represented by the equation 7.

The above-mentioned blood pressure calculating algorithm (ST 22) will be explained below by using a probability density function group.

Figure 7:
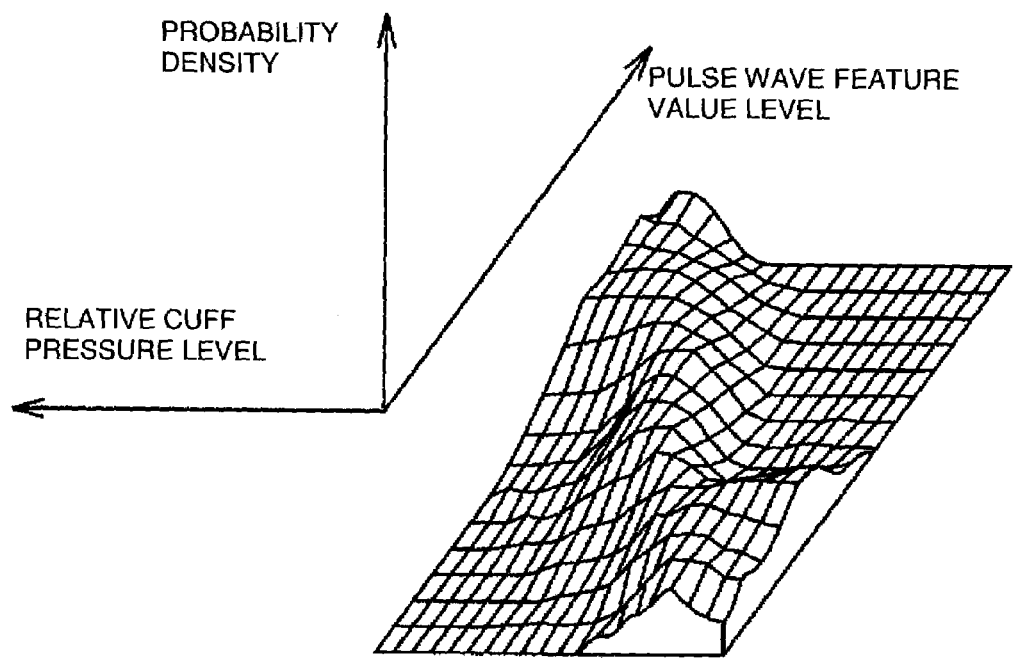
FIG. 7 is a diagram showing a probability density function group according to the embodiment.

The probability density function group in FIG. 7 is used when the pulse wave feature value and the cuff pressure at the pulse wave detected point are used to calculate the blood pressure value, and probability density of the pulse wave feature value is represented for each relative cuff pressure, mentioned later, classified by a rank. The pulse wave feature value and the cuff pressure at the pulse wave detected point are data to be calculated or measured at the time of measuring each blood pressure, and the probability density function group is data previously stored in an internal memory of the MPU 10. Two kinds of the probability density function groups are provided.

The first kind of the probability density function group is referred to when SBP is calculated. The functions of the probability density function group are two-parameter functions defined by using two parameters of the pulse wave feature value and a SBP relative cuff press Prs. The probability density function group independently exist correspondingly to a number of types of the pulse wave feature values. The SBP relative cuff pressure Prs is defined by using a cuff pressure Pc and SBP according to a following equation:

$$Prs = Pc - SBP \qquad \text{Equation (8)}$$

Here, the cuff pressure Pc shows a cuff pressure detected correspondingly to a pulse wave detecting point.

The second type of the probability density function group is referred to when DBP is calculated. The functions of the probability density function group are two-parameter functions having the pulse wave feature value and DBP relative cuff pressure Prd. The probability density function group independently exists correspondingly to a number of types of the pulse wave feature values. The DBP relative cuff pressure Prd is defined by using the cuff pressure Pc and DBP according to a following equation:

$$Prd = Pc - DBP \qquad \text{Equation (9)}$$

The probability density function group is generated by collecting the pulse wave feature value, the cuff pressure at the pulse wave detecting point, SBP and DBP from a lot of subjects. At this time, the data which are used for generating the probability density function group are data which are collected by adjusting the cuff pressure between the lower limit and the upper limit.

Procedures (1) to (4) for estimating SBP and DBP of an arbitrary pulse wave using the probability density function group will be explained below. The procedures are described concretely in Japanese Patent Application 2002-53671 (filed on Feb. 28, 2002) incorporated by reference of the applicants of the present invention, and SBP and DBP are also described therein.

(1) All pulse wave feature values of pulse waves actually measured for calculating a blood pressure (SBP or DBP) are calculated.

(2) The probability density functions at a corresponding rank of the relative cuff pressure are extracted from the corresponding probability density function group based on the calculated pulse wave feature values. Here, for example, the probability density functions in FIGS. 8A to 8D are supposed to be extracted.

Figure 8A:
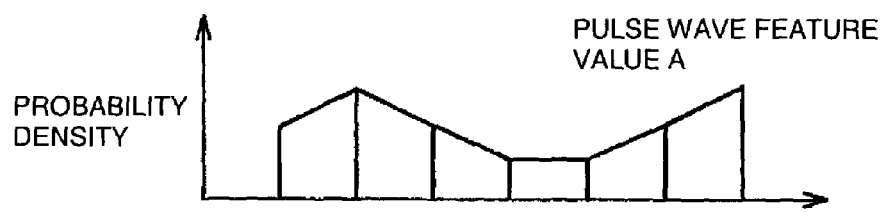
FIGS. 8A to 8D are diagrams showing a procedure for calculating a probability density function and estimating a blood pressure value according to the embodiment.
Figure 8B:
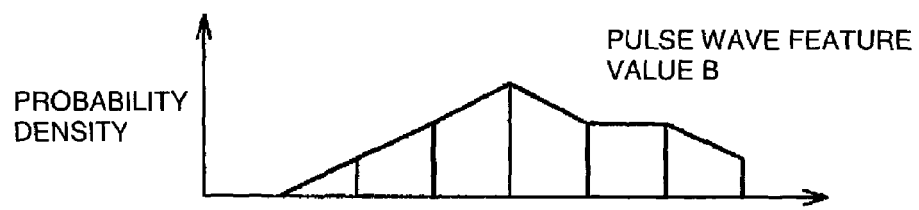
Figure 8C:
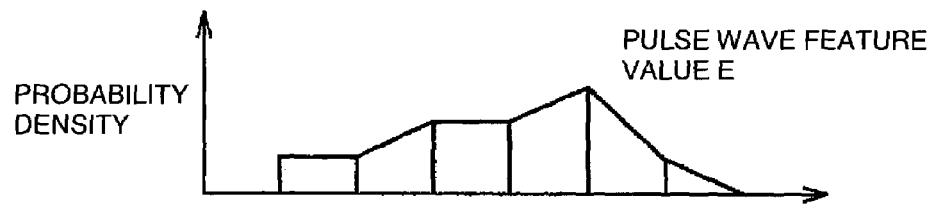
Figure 8D:
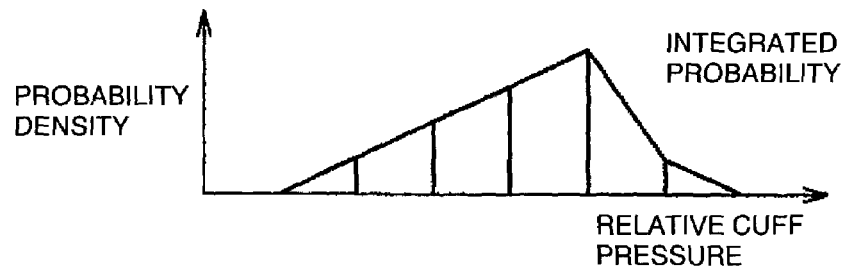

(3) An operation is performed on the extracted probability density functions of the pulse wave feature values at the same rank of the relative cuff pressure, and the obtained function is called as an integrated probability density function (see FIG. 8D). Here, simple multiplication is used for the operation.

(4) The relative cuff pressure corresponding to a maximum value of the integrated probability density function is specified. The specified relative cuff pressure is subtracted from the cuff pressure at the time of detecting the corresponding pulse wave, so that the blood pressure value (SBP, DBP) is estimated (calculated).

[Calculation of the Blood Pressure Value Using Weight]

In the process at ST 21 and ST 22, when the pulse waves are detected, the pulse wave feature values are calculated and the blood pressure value is calculated under a plurality of different cuff pressures, the calculation may be made by using weight in a following manner.

Figure 9A:
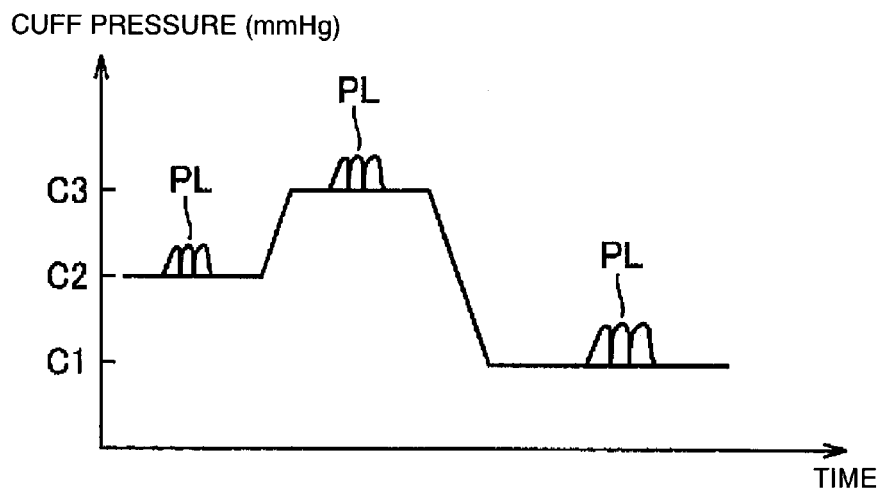
FIGS. 9A to 9C are diagrams showing changes in a cuff pressure according to lapse of time.
Figure 9B:
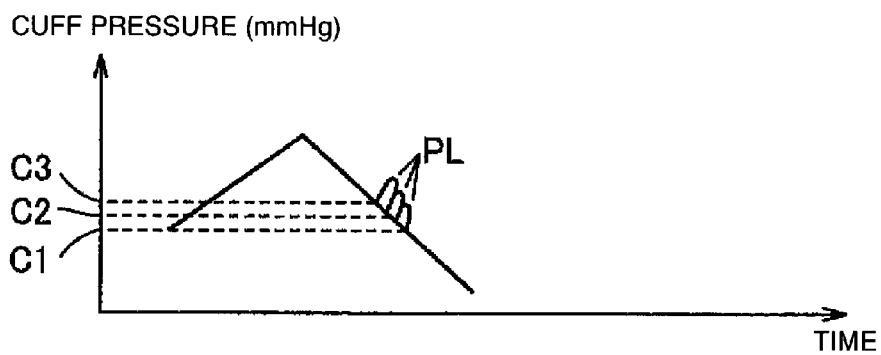
Figure 9C:
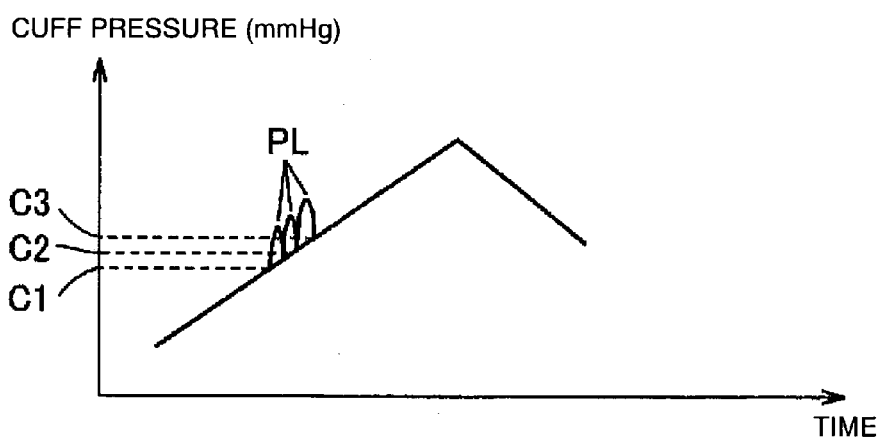

FIGS. 9A to 9C show changes in the cuff pressure according to lapse of the measuring time. In these measurements, the cuff pressure is changed within the range between the upper limit and the lower limit, so that the pulse wave is detected. FIG. 9A shows the case where the cuff pressure is changed gradually as shown in FIG. 5, a pulse wave PL is detected at plural different arbitrary levels of cuff pressures C1, C2 and C3, and the wave feature values of the pulse waves PL are calculated and the blood pressure value is calculated. FIGS. 9B and 9C show the case where when the blood pressure is measured at pressure reducing process and the pressurizing process, the pulse wave PL is detected, the wave feature values of the pulse waves PL are calculated and the blood pressure value is calculated at the plural different arbitrary levels of the cuff pressures C1, C2 and C3.

Namely, in FIGS. 9A to 9C, an attention is paid to that as the cuff pressure at the time of detecting the pulse wave PL is closer to MAP (a difference between them is smaller), the amplitude of the pulse wave PL is larger (the S/N ratio is larger and an error is smaller), and the weight is increased and the calculation is made so that the value with less error effectively affects a calculated result.

More concretely, in the calculation of the blood pressure value at ST 22, as the corresponding cuff pressure is closer to MAP calculated for the pulse wave PL in the pulse waves PL detected under the plural different cuff pressures, weight is further increased, and an average of the blood pressure value (SBP, DBP) is calculated so that the calculated result may be estimated (calculated) as the blood pressure value.

In addition, as the pulse wave amplitude Am of the pulse wave PL calculated at ST 21 is larger, the weight is larger, and the average of the blood pressure value (SBP, DBP) is calculated so that the calculated result may be estimated (calculated) as the blood pressure value.

In the embodiment, the detection of the pulse wave, the calculation of the wave feature value of the pulse wave and the calculation of the blood pressure value from the wave feature value of the pulse wave are carried out within the interval between the set upper limit and lower limit.

A pulse wave in a vicinity of an average blood pressure is used for the detection of the pulse wave, the calculation of the wave feature value of the pulse wave and the calculation of the blood pressure value based on the calculated wave feature value.

When the pulse wave is detected at the plural different cuff pressure levels, the wave feature value of the pulse wave is calculated and the blood pressure value is calculated, the blood pressure values are averaged by an averaging formula of the weight according to the cuff pressure levels of the equation 2. Since the blood pressure is measured according to any one of them or not less than two of them, following characteristics can be obtained.

The blood pressure measuring accuracy is improved. When the measuring interval between the upper limit and the lower limit is specified, an amount of data in the MPU 10 required for the calculation of the blood pressure can be reduced, thereby reducing volume consumption of the memory in the MPU 10.

In the case where a pulse wave with many noise components is used, a process for removing a noise such as a filter process is required conventionally, but in this embodiment, since the pulse wave in the vicinity of the average blood pressure with less noise component is used, the noise removing process is not necessary, thereby realizing the function by mounting an inexpensive microprocessor and a small-capacity memory.

It should be understood that the embodiment disclosed herein is in all aspects illustrative and not restrictive. It is therefore intended that the scope of the present invention is clarified not by the above explanation but by claims, and is intended to include all modifications within the scope of claims and within uniform means and ranges.

According to the present invention, since the detection of the pulse wave, the calculation of the wave feature value of the pulse wave and the calculation of the blood pressure value from the wave feature value of the pulse wave are carried out within the interval between the set upper limit and the lower limit, the noise is suppressed and the blood pressure can be measured with good accuracy.

In addition, since the amplitude of the pulse wave at the average value of the blood pressure or in its vicinity is approximately maximum and the S/N ratio of the pulse wave is high, an error in the operation of the blood pressure is reduced so that the blood pressure measuring accuracy becomes high.

Further, a predetermined level which is suitable for calculating the blood pressure of each subject does not have to be previously known. Moreover, a predetermined level which is suitable for calculating the blood pressure changes according to subjects or conditions of one subject and measuring time, but since the predetermined level is searched at every time of measurement, the high measuring accuracy can be obtained irrespective of dispersion of subjects, conditions of one subject and measuring time.

In addition, an attention is paid to that as the cuff pressure at the time of detecting the pulse wave is closer to the corresponding average blood pressure, the amplitude of the pulse wave is larger, and the weight is increased so that the value with less error effectively affects the operation in the blood pressure calculating unit, thereby suppressing the error included in the operated result in the blood pressure calculating unit.

Further, the weight is increased so that as the S/N ratio is larger or the error is smaller, the calculated amplitude of the pulse wave effectively affects the operation in the blood pressure calculating unit, thereby suppressing the error included in the operated result of the blood pressure calculating unit.

What is claimed is:

1. An electronic blood pressure monitor comprising:
   a cuff configured to be mounted on a predetermined portion of a subject for pressurizing an artery of the subject;
   a cuff pressure controller for controlling a cuff pressure inside the cuff;
   a pressure detector for detecting the cuff pressure;
   a pulse wave detector for detecting a pulse wave of the artery that is pressured by the cuff;
   a wave feature calculating unit for calculating a wave feature value of the pulse wave detected by the pulse wave detector;
   a function memory that stores a two-parameter function having the wave feature value and a relative cuff pressure as parameters, the relative cuff pressure being a pressure difference between the detected cuff pressure and a blood pressure of the subject;
   a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter;
   a relative cuff pressure determining unit that determines the relative cuff pressure corresponding to the pulse wave detected by the pulse wave detector as a maximum of the single-parameter function or a maximum of a function generated based on the single-parameter function; and
   a blood pressure calculating unit that calculates the blood pressure of the subject by subtracting the determined relative cuff pressure from the cuff pressure detected by the pressure detector when the pulse wave detector detects the pulse wave,
   wherein the cuff pressure controller maintains the cuff pressure between an upper limit and a lower limit while the pulse wave detector detects the pulse wave.

2. The electronic blood pressure monitor of claim 1, further comprising a blood pressure averaging unit that calculates an average blood pressure, wherein the cuff pressure controller changes the cuff pressure so that the cuff pressure approaches the average blood pressure when the average blood pressure is not equal to the cuff pressure detected by the pressure detector when the pulse wave detector detects the pulse wave, and the electronic blood pressure monitor calculates the blood pressure of the subject at the cuff pressure changed by the cuff controller.

3. The electronic blood pressure monitor of claim 1, further comprising a blood pressure averaging unit, wherein the pulse wave detector detects a plurality of the pulse waves, and the blood pressure averaging unit calculates an average of the blood pressures of the subject calculated for the plurality of the pulse waves.

4. The electronic blood pressure monitor of claim 1, further comprising a blood pressure comparing unit, wherein the pulse wave detector detects a plurality of the pulse waves, and the blood pressure comparing unit calculates a difference between two of the blood pressures of the subject calculated for the plurality of the pulse waves.

5. The electronic blood pressure monitor of claim 1, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

6. An electronic blood pressure monitor comprising:
   a cuff configured to be mounted on a predetermined portion of a subject for pressurizing an artery of the subject;
   a cuff pressure controller for controlling a cuff pressure inside the cuff;
   a pressure detector for detecting the cuff pressure;
   a pulse wave detector for detecting a pulse wave of the artery that is pressured by the cuff;
   a wave feature calculating unit for calculating a wave feature value of the pulse wave detected by the pulse wave detector;
   a function memory that stores a two-parameter function having the wave feature value and a relative cuff pressure as parameters, the relative cuff pressure being a pressure difference between the detected cuff pressure and a blood pressure of the subject;

a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter;

a relative cuff pressure determining unit that determines the relative cuff pressure corresponding to the pulse wave detected by the pulse wave detector as a maximum of the single-parameter function or a maximum of a function generated based on the single-parameter function;

a blood pressure calculating unit that calculates the blood pressure of the subject by subtracting the determined relative cuff pressure from the cuff pressure detected by the pressure detector when the pulse wave detector detects the pulse wave, and a blood pressure averaging unit that calculates an average blood pressure, wherein the cuff pressure controller changes the cuff pressure so that the cuff pressure approaches the average blood pressure when the average blood pressure is not equal to the cuff pressure detected by the pressure detector when the pulse wave detector detects the pulse wave, and the pulse wave detector detects the pulse wave at the cuff pressure changed by the cuff controller.

7. The electronic blood pressure monitor of claim 6, wherein the cuff pressure controller maintains the cuff pressure between an upper limit and a lower limit while the pulse wave detector detects the pulse wave.

8. The electronic blood pressure monitor of claim 6, wherein the pulse wave detector detects a plurality of the pulse waves, and the blood pressure averaging unit calculates a pulse wave average of the blood pressures of the subject calculated for the plurality of the pulse waves.

9. The electronic blood pressure monitor of claim 6, further comprising a blood pressure comparing unit, wherein the pulse wave detector detects a plurality of the pulse waves, and the blood pressure comparing unit calculates a difference between two of the blood pressures of the subject calculated for the plurality of the pulse waves.

10. The electronic blood pressure monitor of claim 6, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

11. An electronic blood pressure monitor comprising:

a cuff configured to be mounted on a predetermined portion of a subject for pressurizing an artery of the subject;

a cuff pressure controller for controlling a cuff pressure inside the cuff;

a pressure detector for detecting the cuff pressure;

a pulse wave detector for detecting a pulse wave of the artery that is pressured by the cuff;

a wave feature calculating unit for calculating a wave feature value of the pulse wave detected by the pulse wave detector;

a function memory that stores a two-parameter function having the wave feature value and a relative cuff pressure as parameters, the relative cuff pressure being a pressure difference between the detected cuff pressure and a blood pressure of the subject;

a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter;

a relative cuff pressure determining unit that determines the relative cuff pressure corresponding to the pulse wave detected by the pulse wave detector as a maximum of the single-parameter function or a maximum of a function generated based on the single-parameter function; and a blood pressure calculating unit that calculates the blood pressure of the subject by subtracting the determined relative cuff pressure from the cuff pressure detected by the pressure detector when the pulse wave detector detects the pulse wave, wherein the electronic blood pressure monitor uses the calculated blood pressure of the subject to evaluate the cuff pressure detected by the pressure detector when the pulse wave detector detects the pulse wave, changes the cuff pressure to an appropriate value and calculates the blood pressure of the subject at the changed cuff pressure.

12. The electronic blood pressure monitor of claim 11, further comprising a blood pressure averaging unit that calculates an average blood pressure, wherein the cuff pressure controller changes the cuff pressure so that the cuff pressure approaches the average blood pressure when the average blood pressure is not equal to the cuff pressure detected by the pressure detector when the pulse wave detector detects the pulse wave.

13. The electronic blood pressure monitor of claim 11, wherein the cuff pressure controller maintains the cuff pressure between an upper limit and a lower limit while the pulse wave detector detects the pulse wave.

14. The electronic blood pressure monitor of claim 11, further comprising a blood pressure averaging unit, wherein the pulse wave detector detects a plurality of the pulse waves, and the blood pressure averaging unit calculates an average of the blood pressures of the subject calculated for the plurality of the pulse waves.

15. The electronic blood pressure monitor of claim 11, further comprising a blood pressure comparing unit, wherein the pulse wave detector detects a plurality of the pulse waves, and the blood pressure comparing unit calculates a difference between two of the blood pressures of the subject calculated for the plurality of the pulse waves.

16. The electronic blood pressure monitor of claim 11, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

17. An electronic blood pressure monitor comprising:
a cuff configured to be mounted on a predetermined portion of a subject for pressurizing an artery of the subject;
a cuff pressure controller for controlling a cuff pressure inside the cuff;
a pressure detector for detecting the cuff pressure;
a pulse wave detector for detecting a pulse wave of the artery that is pressured by the cuff;
a wave feature calculating unit for calculating a wave feature value of the pulse wave detected by the pulse wave detector for each of a systolic blood pressure and a diastolic blood pressure;
a function memory that stores, for each of the systolic blood pressure and the diastolic blood pressure, a two-parameter function having the wave feature value and a relative cuff pressure as parameters, the relative cuff pressure being a pressure difference between the detected cuff pressure and a blood pressure of the subject;
a single-parameter function generating unit that generates a single-parameter function for each of the systolic blood pressure and the diastolic blood pressure by setting the wave feature value of the corresponding two-parameter function at the corresponding calculated wave feature value of the pulse wave detected by the pulse wave detector so that the single-parameter functions have the relative cuff pressure as a parameter;
a relative cuff pressure determining unit that determines, for each of the systolic blood pressure and the diastolic blood pressure, the relative cuff pressure corresponding to the pulse wave detected by the pulse wave detector as a maximum of the single-parameter function or a maximum of a function generated based on corresponding the single-parameter function;
a blood pressure calculating unit that calculates, for each of the systolic blood pressure and the diastolic blood pressure, the blood pressure of the subject by subtracting the determined relative cuff pressure from the corresponding cuff pressure detected by the pressure detector when the pulse wave detector detects the pulse wave, the blood pressure calculating unit calculating a systolic and diastolic average by averaging the calculated blood pressure corresponding to the systolic blood pressure and the calculated blood pressure corresponding to the diastolic blood pressure, and
a blood pressure averaging unit,
wherein the electronic blood pressure monitor repeats the calculation of the blood pressure of the subject at a plurality of the cuff pressures for each of the systolic blood pressure and the diastolic blood pressure, the blood pressure averaging unit calculates an average of the blood pressures of the subject calculated at the plurality of the cuff pressures for each of the systolic blood pressure and the diastolic blood pressure such that a higher weight is given to the calculated blood pressure having the corresponding systolic and diastolic average closer to the cuff pressure of the corresponding pulse wave detection.

18. The electronic blood pressure monitor of claim 17, wherein the cuff pressure controller maintains the cuff pressure between an upper limit and a lower limit while the pulse wave detector detects the pulse wave.

19. The electronic blood pressure monitor of claims 17, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

20. An electronic blood pressure monitor comprising:
a cuff configured to be mounted on a predetermined portion of a subject for pressurizing an artery of the subject;
a cuff pressure controller for controlling a cuff pressure inside the cuff;
a pressure detector for detecting the cuff pressure;
a pulse wave detector for detecting a pulse wave of the artery that is pressured by the cuff;
a wave feature calculating unit for calculating a wave feature value of the pulse wave detected by the pulse wave detector;
a function memory that stores a two-parameter function having the wave feature value and a relative cuff pressure as parameters, the relative cuff pressure being a pressure difference between the detected cuff pressure and a blood pressure of the subject;
a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter;
a relative cuff pressure determining unit that determines the relative cuff pressure corresponding to the pulse wave detected by the pulse wave detector as a maximum of the single-parameter function or a maximum of a function generated based on the single-parameter function;
a blood pressure calculating unit that calculates the blood pressure of the subject by subtracting the determined relative cuff pressure from the cuff pressure detected by the pressure detector when the pulse wave detector detects the pulse wave; and
a blood pressure averaging unit,
wherein the electronic blood pressure monitor repeats the calculation of the blood pressure of the subject at a plurality of the cuff pressures, the blood pressure averaging unit calculates an average of the blood pressures of the subject calculated at the plurality of the cuff pressures such that a higher weight is given to the blood pressure calculated from the pulse wave having a greater amplitude.

21. The electronic blood pressure monitor of claim 20, wherein the cuff pressure controller maintains the cuff pressure between an upper limit and a lower limit while the pulse wave detector detects the pulse wave.

22. The electronic blood pressure monitor of claims 20, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

23. An electronic blood pressure monitor comprising:
a cuff configured to be mounted on a predetermined portion of a subject for pressurizing an artery of the subject;
a cuff pressure controller for controlling a cuff pressure inside the cuff;
a pressure detector for detecting the cuff pressure;
a pulse wave detector for detecting a pulse wave of the artery that is pressured by the cuff;
a wave feature calculating unit for calculating a wave feature value of the pulse wave detected by the pulse wave detector;
a function memory that stores a two-parameter function having the wave feature value and a relative cuff pressure as parameters, the relative cuff pressure being a pressure difference between the detected cuff pressure and a blood pressure of the subject;
a single-parameter function generating unit that generates a single-parameter function by setting the wave feature value of the two-parameter function at the calculated wave feature value of the pulse wave detected by the pulse wave detector so that the single-parameter function has the relative cuff pressure as a parameter;
a relative cuff pressure determining unit that determines the relative cuff pressure corresponding to the pulse wave detected by the pulse wave detector as a maximum of the single-parameter function or a maximum of a function generated based on the single-parameter function; and
a blood pressure calculating unit that calculates the blood pressure of the subject by subtracting the determined relative cuff pressure from the cuff pressure detected by the pressure detector when the pulse wave detector detects the pulse wave,
wherein the cuff pressure controller and the pressure detector operate to increase the cuff pressure to a predetermined pressure with a predetermined tolerance.

24. The electronic blood pressure monitor of claim 23, further comprising a blood pressure averaging unit that calculates an average blood pressure, wherein the cuff pressure controller changes the cuff pressure so that the cuff pressure approaches the average blood pressure when the average blood pressure is not equal to the cuff pressure detected by the pressure detector when the pulse wave detector detects the pulse wave, and the electronic blood pressure monitor calculates the blood pressure of the subject at the cuff pressure changed by the cuff controller.

25. The electronic blood pressure monitor of claim 23, further comprising a blood pressure averaging unit, wherein the pulse wave detector detects a plurality of the pulse waves, and the blood pressure averaging unit calculates an average of the blood pressures of the subject calculated for the plurality of the pulse waves.

26. The electronic blood pressure monitor of claim 23, further comprising a blood pressure comparing unit, wherein the pulse wave detector detects a plurality of the pulse waves, and the blood pressure comparing unit calculates a difference between two of the blood pressures of the subject calculated for the plurality of the pulse waves.

27. The electronic blood pressure monitor of claim 23, wherein the wave feature calculating unit calculates a plurality of the wave features of the pulse wave, the function memory stores a plurality of the two-parameter functions corresponding to the plurality of the wave features, a single-parameter function generating unit generates a plurality of the single-parameter functions corresponding to the plurality of the two-parameter functions, and the relative cuff pressure determining unit determines the relative cuff pressure as a maximum of a function generated based on the plurality of the single-parameter functions.

* * * * *